United States Patent
Gilbert et al.

(10) Patent No.: US 9,802,767 B2
(45) Date of Patent: Oct. 31, 2017

(54) MULTILAYER HYDRODYNAMIC SHEATH FLOW STRUCTURE

(71) Applicant: CYTONOME/ST, LLC, Boston, MA (US)

(72) Inventors: John R. Gilbert, Brookline, MA (US); Manish Deshpande, Canton, MA (US); Bernard Bunner, Watertown, MA (US)

(73) Assignee: CYTONOME/ST, LLC, Boston, MA (US)

( * ) Notice: Subject to any disclaimer, the term of this patent is extended or adjusted under 35 U.S.C. 154(b) by 0 days.

(21) Appl. No.: 15/269,556

(22) Filed: Sep. 19, 2016

(65) Prior Publication Data
US 2017/0066605 A1 Mar. 9, 2017

Related U.S. Application Data

(63) Continuation of application No. 13/968,962, filed on Aug. 16, 2013, now Pat. No. 9,446,912, which is a
(Continued)

(51) Int. Cl.
*B01F 13/00* (2006.01)
*B65G 51/08* (2006.01)
(Continued)

(52) U.S. Cl.
CPC .......... *B65G 51/08* (2013.01); *B01F 13/0064* (2013.01); *B01L 3/502776* (2013.01);
(Continued)

(58) Field of Classification Search
CPC ........ B01F 13/0062; G01N 2015/1409; G01N 15/1484; B01L 2200/0673; B01L 2200/0636
(Continued)

(56) References Cited

U.S. PATENT DOCUMENTS 3,649,829 A  3/1972  Randolph
4,126,425 A  11/1978  Twigge-Molecey
(Continued)

FOREIGN PATENT DOCUMENTS

WO  9843066 A1  10/1998
WO  9960397 A1  11/1999
(Continued)

OTHER PUBLICATIONS

Australian Patent Examination Report No. 1, Patent Appl. No. 2011205167, dated Jul. 6, 2012.

*Primary Examiner* — Joseph Dillon, Jr.
(74) *Attorney, Agent, or Firm* — McCarter & English, LLP; David R. Burns

(57) ABSTRACT

A microfabricated sheath flow structure for producing a sheath flow includes a primary sheath flow channel for conveying a sheath fluid, a sample inlet for injecting a sample into the sheath fluid in the primary sheath flow channel, a primary focusing region for focusing the sample within the sheath fluid and a secondary focusing region for providing additional focusing of the sample within the sheath fluid. The secondary focusing region may be formed by a flow channel intersecting the primary sheath flow channel to inject additional sheath fluid into the primary sheath flow channel from a selected direction. A sheath flow system may comprise a plurality of sheath flow structures operating in parallel on a microfluidic chip.

20 Claims, 12 Drawing Sheets

Related U.S. Application Data continuation of application No. 13/179,084, filed on Jul. 8, 2011, now Pat. No. 8,529,161, which is a continuation of application No. 12/610,753, filed on Nov. 2, 2009, now Pat. No. 7,997,831, which is a continuation of application No. 11/998,557, filed on Nov. 30, 2007, now Pat. No. 7,611,309, which is a continuation of application No. 10/979,848, filed on Nov. 1, 2004, now Pat. No. 7,311,476.

(60) Provisional application No. 60/516,033, filed on Oct. 30, 2003.

(51) Int. Cl.
  *B01L 3/00* (2006.01)
  *G01N 15/14* (2006.01)
  *B65G 51/00* (2006.01)

(52) U.S. Cl.
  CPC ..... *G01N 15/1404* (2013.01); *G01N 15/1484* (2013.01); *B01F 13/0062* (2013.01); *B01J 2219/0086* (2013.01); *B01J 2219/00822* (2013.01); *B01J 2219/00831* (2013.01); *B01J 2219/00833* (2013.01); *B01J 2219/00891* (2013.01); *B01L 2200/0636* (2013.01); *B01L 2200/0673* (2013.01); *B01L 2300/0816* (2013.01); *B01L 2300/0864* (2013.01); *B01L 2300/0887* (2013.01); *B01L 2400/0487* (2013.01); *B65G 51/00* (2013.01); *G01N 2015/1409* (2013.01)

(58) Field of Classification Search
  USPC ........................................................ 406/198
  See application file for complete search history.

(56) References Cited

U.S. PATENT DOCUMENTS

| | | | |
|---|---|---|---|
| 4,503,385 A | | 3/1985 | Haynes |
| 4,752,131 A | * | 6/1988 | Eisenlauer ............ C02F 1/5209 250/564 |
| 4,756,427 A | | 7/1988 | Gohde et al. |
| 4,844,610 A | | 7/1989 | North, Jr. |
| 4,954,715 A | | 9/1990 | Zold |
| 4,983,038 A | | 1/1991 | Ohki et al. |
| 5,030,002 A | | 7/1991 | North, Jr. |
| 5,040,890 A | | 8/1991 | North, Jr. |
| 5,311,290 A | | 5/1994 | Olson et al. |
| 5,521,079 A | | 5/1996 | Dorian et al. |
| 5,808,737 A | | 9/1998 | Edens et al. |
| 5,880,835 A | * | 3/1999 | Yamazaki ............ G01N 15/147 356/336 |
| 5,902,745 A | | 5/1999 | Butler et al. |
| 6,159,739 A | | 12/2000 | Weigl et al. |
| 6,365,106 B1 | | 4/2002 | Nagai |
| 6,473,171 B1 | | 10/2002 | Buttry et al. |
| 6,475,364 B1 | | 11/2002 | Dubrow et al. |
| 6,506,609 B1 | | 1/2003 | Wada et al. |
| 6,537,501 B1 | | 3/2003 | Holl et al. |
| 6,576,194 B1 | | 6/2003 | Holl et al. |
| 6,592,821 B1 | | 7/2003 | Wada et al. |
| 6,674,525 B2 | | 1/2004 | Bardell et al. |
| 6,710,874 B2 | | 3/2004 | Mavliev |
| 6,890,093 B2 | | 5/2005 | Karp et al. |
| 7,116,407 B2 | | 10/2006 | Hansen et al. |
| 7,157,274 B2 | | 1/2007 | Bohm et al. |
| 7,223,371 B2 | | 5/2007 | Hayenga et al. |
| 7,242,474 B2 | | 7/2007 | Cox et al. |
| 7,311,476 B2 | | 12/2007 | Gilbert et al. |
| 7,355,696 B2 | | 4/2008 | Mueth et al. |
| 7,402,131 B2 | | 7/2008 | Mueth et al. |
| 7,419,784 B2 | | 9/2008 | Dubrow et al. |
| 7,434,982 B2 | * | 10/2008 | Nagasawa ............ B01F 5/0453 366/147 |
| 7,442,339 B2 | | 10/2008 | Sundararajan et al. |
| 7,452,726 B2 | | 11/2008 | Chou et al. |
| 7,553,453 B2 | | 6/2009 | Gu et al. |
| 7,611,309 B2 | | 11/2009 | Gilbert et al. |
| 7,638,339 B2 | | 12/2009 | Sundararajan et al. |
| 7,641,856 B2 | | 1/2010 | Padmanabhan et al. |
| 7,751,040 B2 | | 7/2010 | Chang et al. |
| 7,760,351 B2 | | 7/2010 | Cox et al. |
| 7,772,287 B2 | * | 8/2010 | Higuchi ................ B01F 3/0807 137/3 |
| 7,776,268 B2 | | 8/2010 | Rich |
| 7,802,686 B2 | | 9/2010 | Takagi et al. |
| 7,833,421 B2 | | 11/2010 | Huymann |
| 7,850,907 B2 | | 12/2010 | Sundararajan |
| 7,993,934 B2 | | 8/2011 | Tabata et al. |
| 7,997,831 B2 | | 8/2011 | Gilbert et al. |
| 8,263,387 B2 | | 9/2012 | Pagano et al. |
| 8,383,043 B2 | | 2/2013 | Padmanabhan et al. |
| 8,426,159 B2 | | 4/2013 | Balagadde et al. |
| 8,529,161 B2 | | 9/2013 | Gilbert et al. |
| 8,651,138 B2 | * | 2/2014 | Villarruel ............... G01N 21/05 137/2 |
| 8,961,904 B2 | * | 2/2015 | Xia ........................ F04B 43/095 417/413.2 |
| 9,486,757 B2 | * | 11/2016 | Romanowsky ....... B01F 3/0807 |
| 2002/0097633 A1 | | 7/2002 | O'Connor et al. |
| 2002/0149766 A1 | | 10/2002 | Bardell et al. |
| 2004/0120856 A1 | | 6/2004 | Andersson et al. |
| 2006/0113190 A1 | | 6/2006 | Kurnik |
| 2007/0014695 A1 | | 1/2007 | Yue et al. |
| 2009/0126516 A1 | | 5/2009 | Yamamoto et al. |
| 2012/0097633 A1 | | 4/2012 | Marsollier |
| 2012/0196314 A1 | | 8/2012 | Nawaz et al. |
| 2017/0102381 A1 | * | 4/2017 | Griffiths ............ G01N 33/5432 |

FOREIGN PATENT DOCUMENTS

| | | |
|---|---|---|
| WO | 00/70080 A1 | 11/2000 |
| WO | 03078972 A1 | 9/2003 |
| WO | 2005/042137 A2 | 5/2005 |
| WO | 2015/009284 A1 | 1/2015 |

* cited by examiner

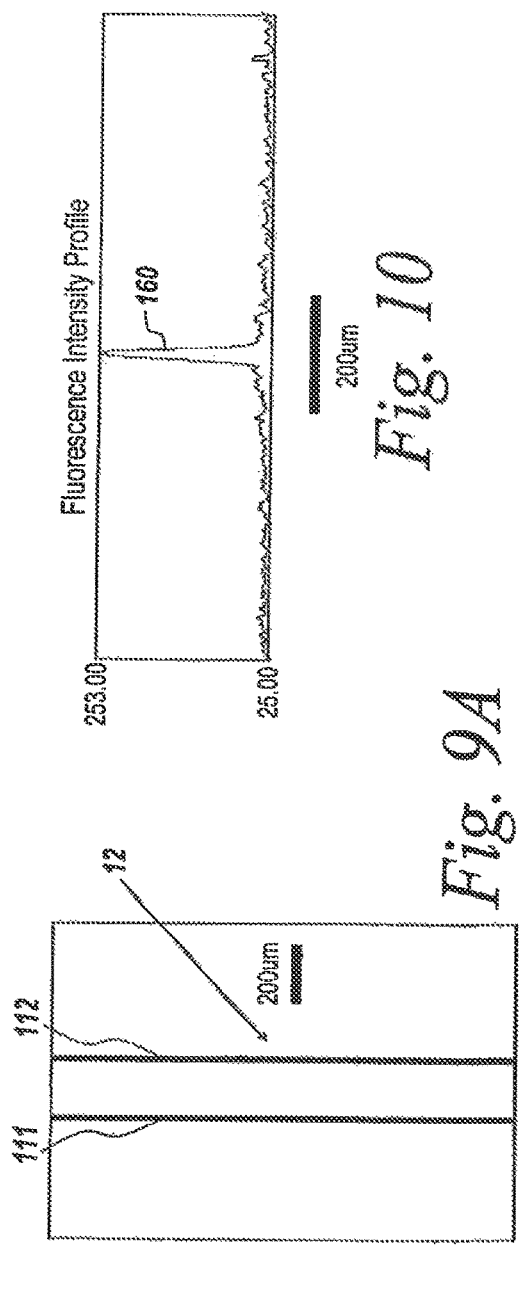

MULTILAYER HYDRODYNAMIC SHEATH FLOW STRUCTURE

RELATED APPLICATIONS

The present invention is a continuation of U.S. patent application Ser. No. 13/968,962, filed Aug. 16, 2013, and is a continuation of U.S. patent application Ser. No. 13/179,084, filed Jul. 8, 2011 and is a continuation application of U.S. patent application Ser. No. 12/610,753, now U.S. Pat. No. 7,997,831, entitled "Multilayer Hydrodynamic Sheath Flow Structure" filed Nov. 2, 2009 and is a continuation application of U.S. patent application Ser. No. 11/998,557, now U.S. Pat. No. 7,611,309, entitled "Multilayer Hydrodynamic Sheath Flow Structure" filed Nov. 30, 2007, which, in turn, is a continuation application of U.S. patent application Ser. No. 10/979,848, now U.S. Pat. No. 7,311,476, entitled, "Multilayer Hydrodynamic Sheath Flow Structure" filed Nov. 1, 2004, which claims priority to U.S. Provisional Application Ser. No. 60/516,033, filed Oct. 30, 2003, the entire content of each application is herein incorporated by reference in their entirety.

FIELD OF THE INVENTION

The present invention relates to a system and method for producing a sheath flow in a flow channel. More particularly, the present invention relates to a system and method for producing a sheath flow in a microchannel in a microfluidic device.

BACKGROUND OF THE INVENTION

Sheath flow is a particular type of laminar flow in which one layer of fluid, or a particle, is surrounded by another layer of fluid on more than one side. The process of confining a particle stream in a fluid is referred to as a 'sheath flow' configuration. For example, in sheath flow, a sheath fluid may envelop and pinch a sample fluid containing a number of particles. The flow of the sheath fluid containing particles suspended therein may be narrowed almost to the outer diameter of particles in the center of the sheath fluid. The resulting sheath flow flows in a laminar state within an orifice or channel so that the particles are lined and accurately pass through the orifice or channel in a single file row.

Sheath flow is used in many applications where it is preferable to protect particles or fluids by a layer of sheath fluid, for example in applications wherein it is necessary to protect particles from air. For example, particle sorting systems, flow cytometers and other systems for analyzing a sample, particles to be sorted or analyzed are usually supplied to a measurement position in a central fluid current, which is surrounded by a particle free liquid sheath.

Sheath flow is useful because it can position particles with respect to sensors or other components and prevent particles in the center fluid, which is surrounded by the sheath fluid, from touching the sides of the flow channel and thereby prevents clogging of the channel. Sheath flow allows for faster flow velocities and higher throughput of sample material. Faster flow velocity is possible without shredding cells in the center fluid because the sheath fluid protects the cells from shear forces at the walls of the flow channel.

Conventional devices that have been employed to implement sheath flow have relatively complex designs and are relatively difficult to fabricate.

SUMMARY OF THE INVENTION

The present invention provides a microfabricated sheath flow structure for producing a sheath flow for a particle sorting system or other microfluidic system. The sheath flow structure may comprise a two-layer construction including a sheath inlet for introducing a sheath fluid into a primary sheath flow channel and a sample inlet for introducing a sample to the structure. A sample is introduced to the sheath fluid in the primary sheath flow channel via the sample inlet and suspended therein. The primary sheath flow channel may branch at a location upstream of a sample inlet to create a flow in an upper sheath channel. The primary sheath flow channel forms a primary focusing region for accelerating sheath fluid in the vicinity of a sample channel connected to the sample inlet. The sample channel provides the injected sample to the accelerating region, such that the particles are confined in the sheath fluid. The primary focusing region further focuses the sheath fluid around the sample. The sheath flow then flows to a secondary sheath region downstream of the primary accelerating region connects the upper sheath channel to the primary sheath flow channel to further focus the sample in the sheath fluid. The resulting sheath flow forms a focused core of sample within a channel.

The sheath flow structure may be parallelized to provide a plurality of sheath flow structures operating in parallel in a single system. The parallelized system may have a single sample inlet that branches into a plurality of sample channels to inject sample into each primary sheath flow channel of the system. The sample inlet may be provided upstream of the sheath inlet. Alternatively, the parallelized system may have multiple sample inlets. The parallelized sheath flow structure may have a single sheath fluid inlet for providing sheath fluid to all of the primary sheath flow channels and/or secondary sheath channels, or multiple sheath fluid inlets for separately providing sheath fluid to the primary sheath flow channels and or secondary sheath channels.

According to a first aspect of the invention, a sheath flow structure for suspending a particle in a sheath fluid is provided. The sheath flow structure comprises a primary sheath flow channel for conveying a sheath fluid, a sample inlet for injecting a particle into the sheath fluid conveyed through the primary sheath flow channel, a primary focusing region for focusing the sheath fluid around the particle in at least a first direction and a secondary focusing region provided downstream of the primary focusing region. The secondary focusing region focuses the sheath fluid around the particle in at least a second direction different from the first direction.

According to another aspect of the invention, a sheath flow structure for suspending a particle in a sheath fluid comprises a first substrate layer including a primary sheath flow channel for conveying a sheath fluid and a second substrate layer stacked on the first substrate layer. The second substrate layer includes a first sheath inlet for introducing a sheath fluid to the primary sheath flow channel, a sample inlet downstream of the first sheath inlet for providing the particle to the primary sheath flow channel in a primary focusing region to form a sheath flow including the particle surrounded by the sheath fluid on at least one side. A first secondary sheath channel is formed in the first or second substrate layer in communication with the primary sheath flow channel. The first secondary sheath channel diverts a portion of said sheath fluid from the primary sheath flow channel.

According to still another aspect of the invention, a focusing region for focusing a particle suspended in a sheath fluid in a channel of a sheath flow device is provided. The focusing region comprises a primary flow channel for conveying a particle suspended in a sheath fluid and a first secondary flow channel intersecting the primary flow path for injecting sheath fluid into the primary flow channel from above the particle to focus the particle away from a top wall of the primary flow channel.

According to another aspect of the invention, a method of surrounding a particle on at least two sides by a sheath fluid, comprises the steps of injecting a sheath fluid into a primary sheath flow channel diverting a portion of the sheath fluid into a branching sheath channel, injecting the particle into the primary sheath flow channel to suspend the particle in the sheath fluid to form a sheath flow and injecting the diverted portion of the sheath fluid into the sheath flow to focus the particle within the sheath fluid.

According to another aspect of the invention, a method of surrounding a particle on at least two sides by a sheath fluid, comprises the steps of conveying a sheath fluid through a primary sheath flow channel, injecting a particle into the sheath fluid conveyed through the primary sheath flow channel, focusing the sheath fluid around the particle in at least a first direction and focusing the sheath fluid around the particle in at least a second direction different from the first direction.

According to still another aspect, a sheath flow system is provided which comprises a plurality of a sheath flow structures operating in parallel on a substrate. Each sheath flow structure comprises a primary sheath flow channel for conveying a sheath fluid, a sample channel for injecting a particle into the sheath fluid conveyed through the primary sheath flow channel, a primary focusing region for focusing the sheath fluid around the particle in at least a first direction and a secondary focusing region provided downstream of the primary focusing region for focusing the sheath fluid around the particle in at least a second direction different from the first direction.

BRIEF DESCRIPTION OF THE FIGURES

FIG. 9A is a fluorescent microscope image of a primary sheath flow channel downstream from the secondary focusing region in the parallelized sheath flow system of FIGS. 8A and 8B.

FIG. 9B is fluorescent microscope image taken of a sample in the primary sheath flow channel of FIG. 9A after focusing of the sample.

FIG. 10 is a histogram diagramming the measured amount of fluorescence in the channel observed in FIG. 9B across axis —A-A—.

DETAILED DESCRIPTION OF THE INVENTION

The present invention provides a system and method for producing a sheath flow in a flow channel, such as a microchannel. The present invention will be described below relative to illustrative embodiments. Those skilled in the art will appreciate that the present invention may be implemented in a number of different applications and embodiments and is not specifically limited in its application to the particular embodiments depicted herein.

As used herein, the term "microfluidic" refers to a system or device for handling, processing, ejecting and/or analyzing a fluid sample including at least one channel having microscale dimensions.

The terms "channel" and "flow channel" as used herein refers to a pathway formed in or through a medium that allows for movement of fluids, such as liquids and gases. A "microchannel" refers to a channel in the microfluidic system preferably have cross-sectional dimensions in the range between about 1.0 µm and about 500 µm, preferably between about 25 µm and about 250 µm and most preferably between about 50 µm and about 150 µm. One of ordinary skill in the art will be able to determine an appropriate volume and length of the flow channel. The ranges are intended to include the above-recited values as upper or lower limits. The flow channel can have any selected shape or arrangement, examples of which include a linear or non-linear configuration and a U-shaped configuration.

Figure 1:
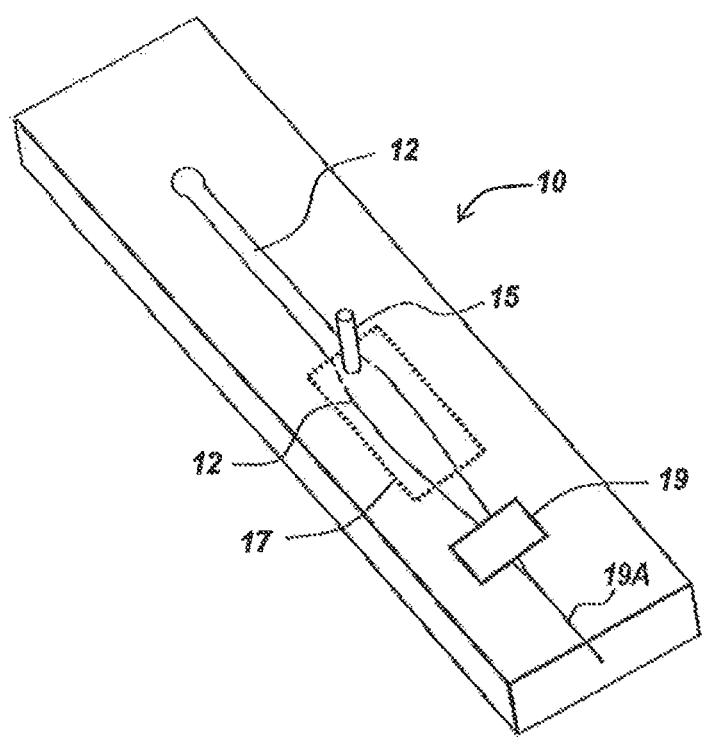
FIG. 1 illustrates a sheath flow structure according to an illustrative embodiment of the invention.

FIG. 1 illustrates a microfabricated sheath flow structure 10 according to an illustrative embodiment of the invention. The sheath flow structure 10 may be used to suspend particles in a sheath fluid flow stream for use in a particle sorting system or other microfluidic system. The sheath flow structure 10 includes a primary sheath flow channel 12 for conveying sheath fluid through the sheath flow structure 10. A flow may be induced through the primary sheath flow channel 12 through any means known in the art, including one or more pumps. The sheath flow structure 10 further includes a sample inlet 15 for introducing a sample, such as one or more particles, to the sheath fluid flowing through the primary sheath flow channel 12, so that the sample is surrounded by the flowing sheath fluid. The sample inlet 15 may comprise a channel, reservoir or other suitable component in communication with the primary sheath flow channel 12.

According to one embodiment, the microfabricated sheath flow structure is formed on a microfluidic chip and the primary sheath flow channel and other flow channels formed therein are microchannels having microscale dimensions. However, one skilled in the art will recognize that the sheath flow structure may alternatively have larger dimensions and be formed using flow channels having cross-sectional dimensions greater than 500 μm. The illustrative sheath flow structure can be fabricated in glass, plastics, metals or any other suitable material using microfabrication, injection molding/stamping, machining or other suitable fabrication technique.

After introduction of the sample into the sheath fluid, a primary focusing region 17 accelerates and focuses the sheath fluid around the injected sample. Preferably, the primary focusing region 17 focuses the sheath fluid away from the sides and bottom of the sample. A secondary focusing region 19, disposed downstream of the primary focusing region 17 along the primary sheath flow channel, provides additional focusing of the sheath fluid around the sample after the primary focusing region performs the primary focusing. Preferably, the secondary focusing region 19 focuses the sample in a vertical direction from above the sample.

According to an illustrative embodiment, the combination of the primary focusing region 17 and the secondary focusing region 19 provides three-dimensional focusing of the sheath fluid around the sample. The resulting sheath flow is sample-focused hydrodynamically on all sides of the sample away from the walls of the primary sheath flow channel 12, with the sample being suspended as a focused core in the approximate center of the channel.

The secondary focusing region 19 passes the resulting sheath flow in the primary sheath flow channel 12 to a particle sorting system or other microfluidic system or component in fluid communication with an outlet 19a of the secondary focusing region 19. The microfluidic system for receiving the sheath flow may be formed on the same chip or substrate as the sheath flow structure or a different substrate in fluid communication with the sheath flow structure 10.

Figure 2A:
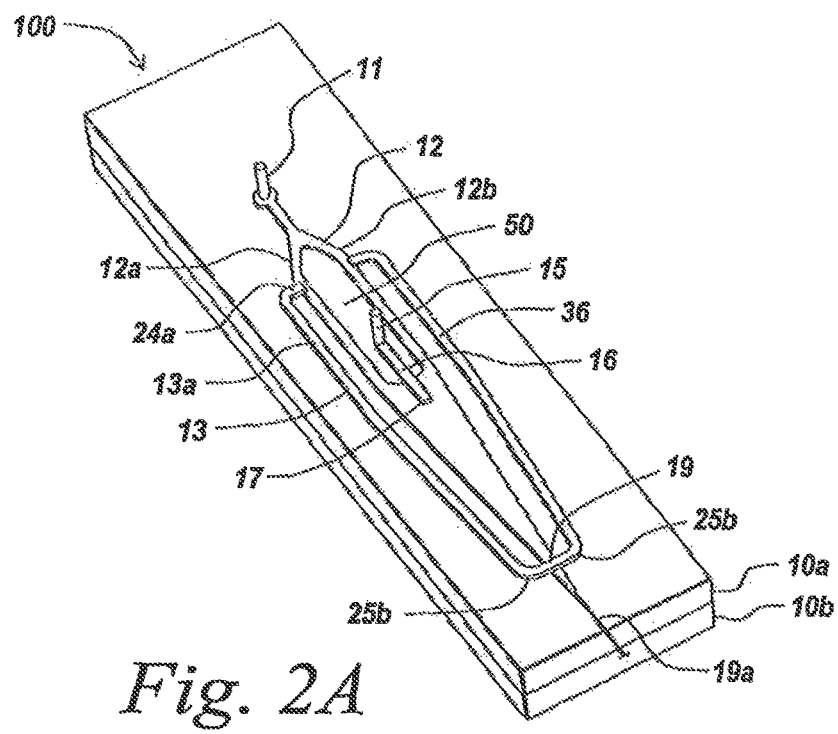
FIGS. 2A-2B illustrate a multilayer sheath flow structure according to an illustrative embodiment of the invention.
Figure 2B:
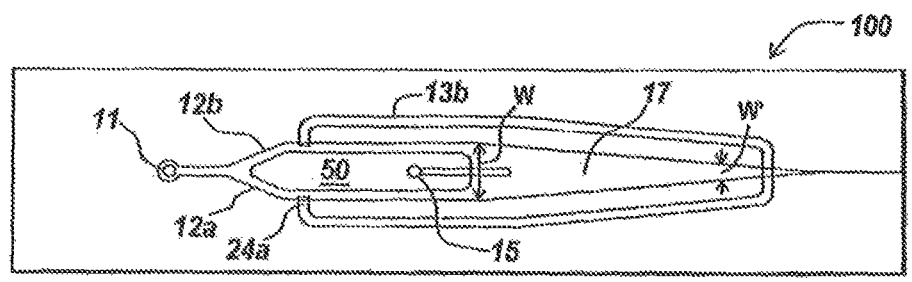
Figure 2C:
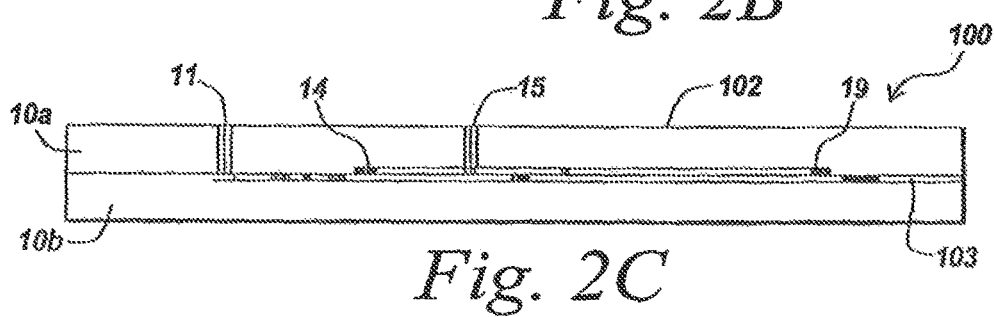
FIG. 2C illustrates is a cross sectional view through the centerline of the sheath flow structure of FIG. 2A, showing the path of an injected particle through the structure.

According to one embodiment, the sheath flow structure may be formed using a plurality of stacked layers. For example, FIGS. 2A-2C illustrate a two-layer sheath flow structure 100 for producing sheath flow according to one embodiment of the invention. In FIGS. 1 and 2A-2C, similar parts are indicated by equivalent reference numbers. The illustrated sheath flow structure 100 has a two-layer construction including a bottom substrate layer 10b and a top substrate layer 10a stacked on the bottom substrate layer 10b. Those of ordinary skill will recognize that any suitable number of layers can be used. The top substrate layer 10a may have formed therein a sheath inlet 11 for introducing a sheath fluid to the primary sheath flow channel 12 and a sample inlet 15 for introducing a sample to the sheath flow structure. The primary sheath flow channel 12 for conveying the sheath fluid through the structure is formed in the bottom layer 10b of the two-layer sheath flow structure 100. As shown, the sample inlet 15 connects to a sample channel 16, which intersects the primary sheath flow channel 12 downstream of the sheath inlet 11 to inject a sample, such as a stream of particles, into a sheath fluid flowing in the primary sheath flow channel 12.

While the illustrative two-layer sheath flow structure 100 injects the sheath flow and sample particles from a top surface of the structure, one skilled in the art will recognize that the sheath inlet 11 and sample inlet 15 can be provided in any suitable location and have any suitable size and configuration.

The primary focusing region 17 in the two-layer sheath flow structure 100 of FIGS. 2A-2C may be formed by tapering the primary sheath flow channel 12 from a relatively wide width W to a smaller width W' downstream of the intersection between the sample channel 16 and the primary sheath flow channel 12, as shown in FIG. 2B. The height of the channel may be substantially constant throughout the length of the channel or may be varied to facilitate focusing of the sample within the sheath fluid.

In the embodiment shown in FIG. 2A, the primary focusing region 17 is formed by dividing the primary sheath flow channel 12 into two subchannels 12a, 12b upstream from the sample inlet 15. The diverging subchannels 12a, 12b form a sample injection island 50 therebetween. At the downstream end of the sample injection island 50, the subchannels 12a, 12b merge to form the primary focusing region 17. The sample flow channel 16 projects into the primary focusing region 17 to convey the sample particles provided via the sample inlet 15 to the primary focusing region 17, such that the sample particles are suspended in the sheath fluid. Alternatively, each of the subchannels 12a, 12b may have a separate inlet, and the separated subchannels may converge in the primary focusing region 17.

In the primary focusing region 17, the sample particles injected into the sheath flow are focused away from the sides and bottom by the sheath flow. As shown, the outlet of the sample flow channel 16 is in substantially the middle of the primary focusing region 17, between the outlets of the subchannels 12a, 12b, such that the particles are surrounded by sheath fluid flowing from the subchannels on both sides of the injected particles and centralized within the sheath fluid flow. The sheath flow channel 12 in the primary focusing region then tapers from a relatively wide width W at the outlets of the subchannels 12a, 12b to a smaller width W' to force the sheath fluid around the suspended sample particles.

After suspension of the sample particles, the sheath flow then flows from the primary focusing region 17 through the sheath flow channel 12, which forms the secondary focusing region 19 downstream of the primary focusing region 17. According to an illustrative embodiment, the secondary focusing region 19 utilizes sheath fluid to provide secondary focusing of the sheath flow in a vertical direction after the initial focusing provided by the primary focusing region 17. For example, as shown in FIGS. 2A-2C, the secondary focusing region 19 may be formed by secondary sheath channels 13a, 13b that intersect the primary sheath flow channel 12 in the secondary focusing region 19. The secondary sheath channels 13a, 13b flow and inject sheath fluid into the primary sheath flow channel 12 to focus the sample within the sheath fluid.

As shown, the inlets to the secondary sheath channels 13a, 13b, respectively, may intersect the primary sheath flow channel 12 in an intermediate upstream region between the sheath inlet 11 and the outlet of the sample channel 16. Branch points 24a, 24b connect each of the secondary sheath channels 13a, 13b to the primary channel 12 to divert a portion of the sheath fluid from the primary sheath flow channel to each of the secondary sheath channels 13a, 13b, respectively. The diverted sheath flow then flows to the secondary focusing region 19, where the outlets of the secondary sheath channels 13a, 13b intersect the primary sheath flow channel 12. Preferably, the outlets of both secondary sheath channels extend above and substantially parallel to the fluid flow in the primary sheath flow channel 12 in the vicinity of the secondary focusing region 19. In this manner, secondary sheath fluid from the secondary sheath channels 13a, 13b enters the primary sheath flow channel 12 from the same side as the sample, compressing the suspended sample away from the upper wall of the channel 12 (i.e., in the other direction from the main sheath of fluid around the particle).

In the illustrative embodiment, branch points 24a, 24b extend substantially transverse or perpendicular to the primary sheath flow channel, while sheath channels 13a, 13b connected to the branch points 24a, 24b, respectively, extend substantially parallel to the primary sheath flow channel 12. Connection branches 25a, 25b for connecting the sheath channels 13a, 13b, respectively, to the primary sheath flow channel in the secondary focusing region 19 may be parallel to the branch points 24a, 24b to create a flow path that is substantially reverse to the direction of the flow path through the branch points 24a, 24b, while the outlets inject the secondary sheath fluid along a path that is above and substantially parallel to fluid flow in the primary sheath flow channel 12.

In the embodiment of FIGS. 2A-2C, the secondary sheath channels 13a, 13b are formed in the upper substrate layer 10a and placed into communication with the primary sheath flow channel 12 in the lower substrate layer 10b when the upper substrate layer 10a is stacked on the lower substrate layer. However, in another embodiment of the invention, one or both of the secondary sheath channels can be formed in the lower substrate layer to provide focusing from any suitable direction.

While the illustrative embodiment includes two branch points 24a, 24b, each connecting to a respective secondary sheath flow channel 13a, 13b extending on opposite sides of the primary sheath flow channel 12, one skilled in the art will recognize that the sheath flow structure of the present invention may include any suitable number of secondary sheath channels having any suitable size, location and configuration.

FIG. 2C is a cross-sectional side view of the sheath flow structure 100 comprising a stacked upper substrate layer and a lower substrate layer. As shown, the primary sheath flow channel may be formed as an open channel in a top surface of the lower substrate layer 10b. The sheath inlet 11 and the sample inlet 15 each extend through the upper substrate layer 10a from one surface 102 of the upper substrate layer 10a to the opposite surface 103. When the upper substrate layer 10a is stacked on the lower substrate layer 10b, the sheath inlet 11 and sample inlet 15 are placed in communication with the primary sheath flow channel 12. The bottom surface 103 of the upper substrate layer 10a may further serve to enclose the primary sheath flow channel 12 when the two substrate layers are stacked together. As also shown, the stacking of the upper substrate layer places the inlet and outlet of each of the secondary sheath channels 13a, 13b in communication with the primary sheath flow channel 12.

The substrate layers 10a, 10b can be machined, molded or etched to form the channels inlets and focusing regions. Suitable materials for forming the substrates 10a, 10b include, but are not limited to silicon wafer, plastic, glass and other materials known in the art.

Figure 3:
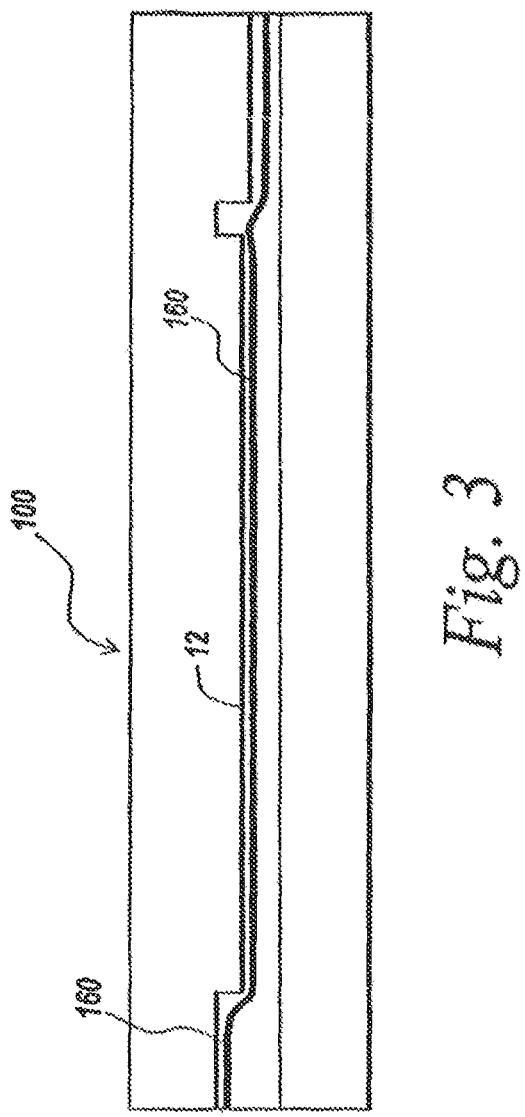
FIG. 3 illustrates the path of a particle through the multilayer sheath flow structure of FIGS. 2A-2C.
Figure 4A:
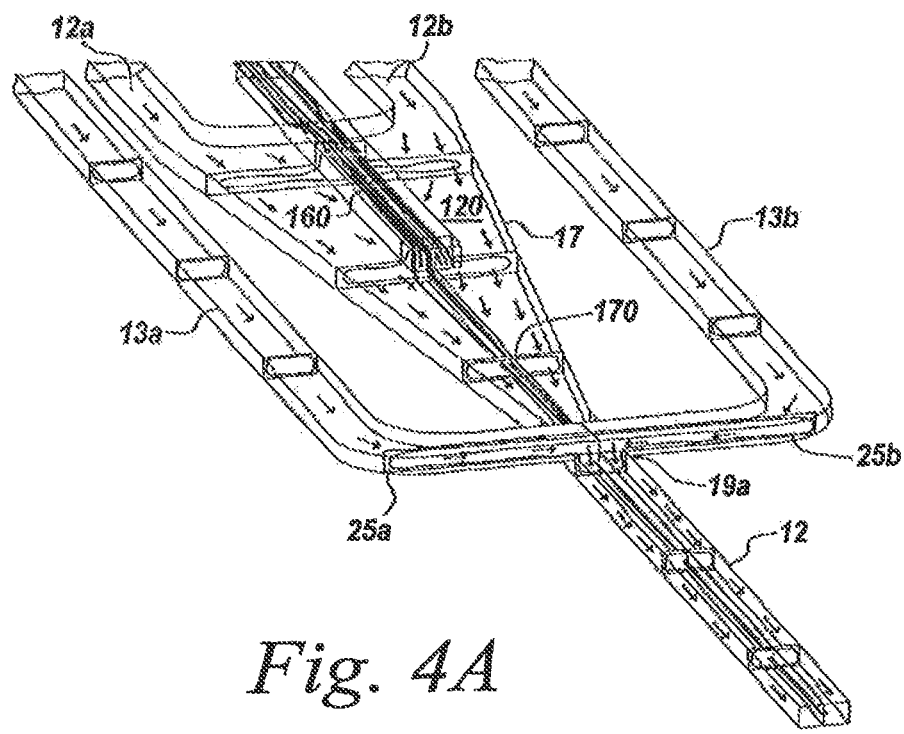
FIG. 4A illustrates the flow profile within the primary focusing region and the secondary focusing region during operation of the sheath flow structure of FIGS. 2A-2C.
Figure 4B:
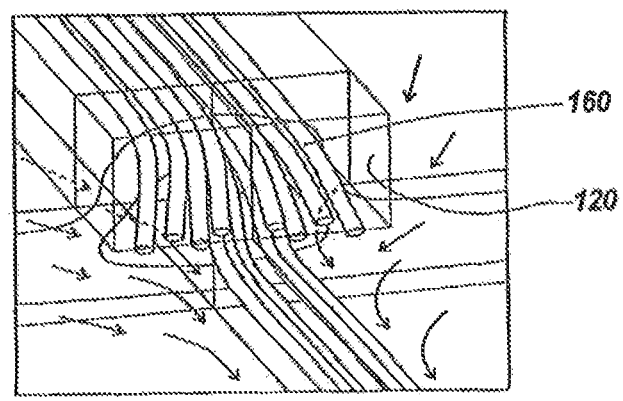
FIGS. 4B-4D are detailed cross-sectional views of the flow profiles within the primary sheath flow channel at different stages during operation of the sheath flow structure of FIGS. 2A-2C.
Figure 4C:
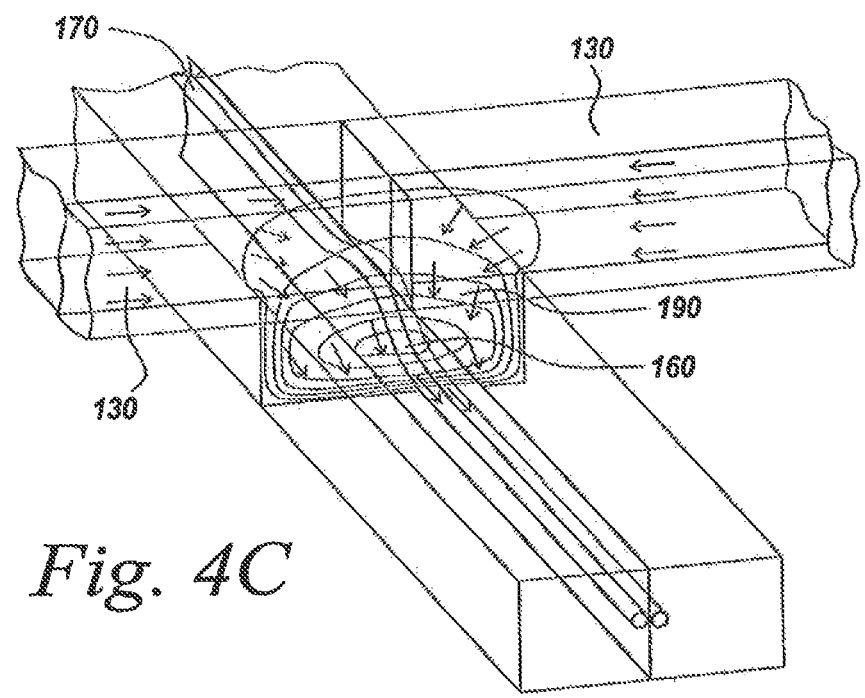
Figure 4D:
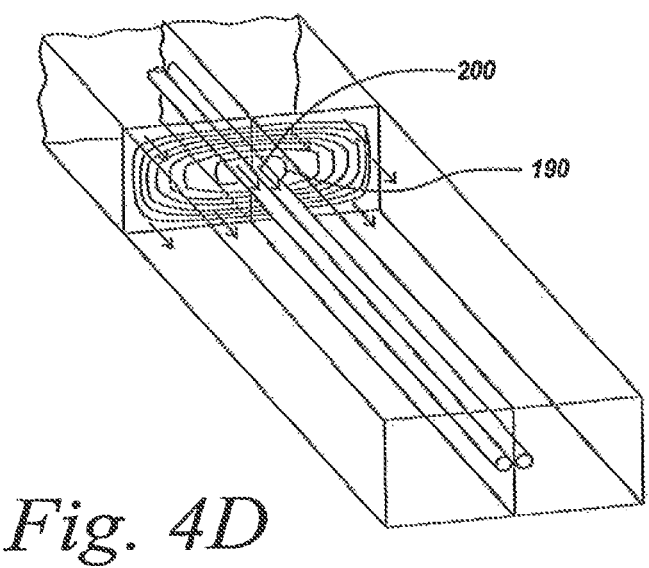

FIG. 3 is a cross-sectional view of the sheath flow structure 100 illustrating the path of a sample particle injected into the sheath flow structure according to the teachings of the present invention. FIG. 4A is a perspective cross-sectional view of the sheath flow structure 100 illustrating the sheath fluid and suspending particle during the different stages of producing a sheath flow. FIGS. 4B-4D are cross-sectional detailed views of the primary flow channel 12 during the different stages of producing a sheath flow. As shown in FIG. 4B, sample 160 from the sample inlet 15 enters the primary focusing region 17 through the sample channel 16 connected to the sample inlet 15 and is focused on three sides by accelerating sheath fluid 120 flowing from the secondary sheath channels into the sheath channel 12 in the primary focusing region 17. The resulting focused flow 170, having the particles suspended therein, passes to the secondary focusing region 19. Additional sheath fluid 130 enters the primary sheath flow channel 12 through a connector in the secondary focusing region 19 to focus the suspended particles on the fourth side, forming a central core 190, as shown in detail in FIG. 4C. The resulting sheath flow 200 is a laminar flow that is sample focused hydrodynamically from all sides away from the walls at the channel center, as shown in FIG. 4D. The desirable core flow location may or may not be at center of the primary sheath flow channel downstream of the secondary sheath flow structure.

In the illustrative embodiment, the flow resistance ratio between the primary sheath flow channel 12 and the branched secondary sheath channels 13a, 13b is calibrated to position the core at specific region in the downstream sheath flow channel. The desirable core flow location may or may not be at center of downstream channel.

Figure 5A:
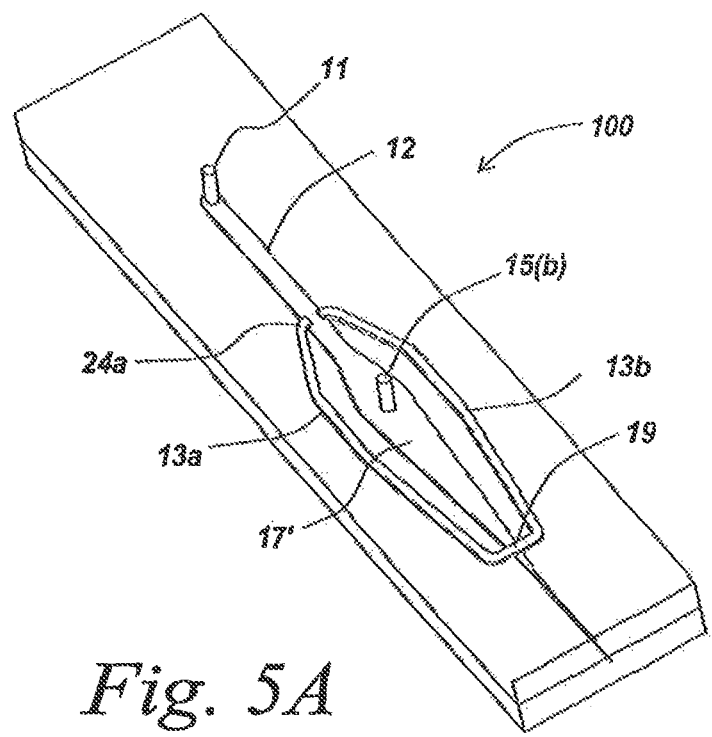
FIGS. 5A-5C illustrates a multilayer sheath flow structure according to an alternate embodiment of the invention, where a sample is injected directly into a focusing region.
Figure 5B:
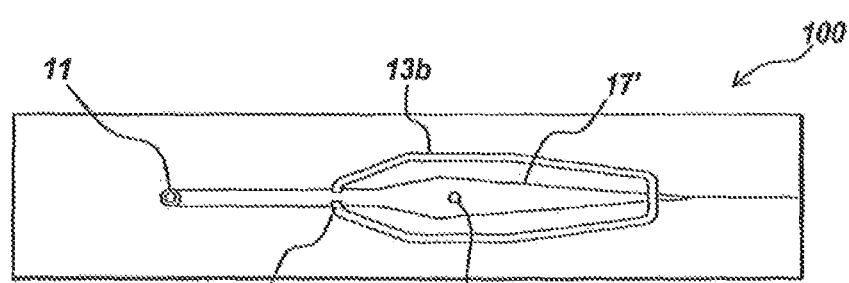
Figure 5C:
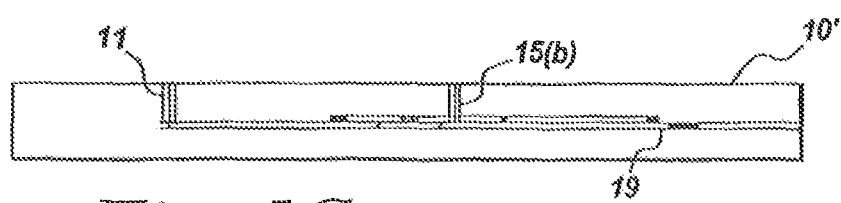

According to an alternate embodiment of the invention, shown in FIGS. 5A-5C, in which like parts are indicated by like reference numbers, the sample can be injected directly from a sample inlet 15b into a primary focusing region 17', which is formed by a widening of the sheath channel 12 downstream of the branch points 24a, 24b. The primary sheath flow channel 12 conveys the sheath fluid directly to the primary focusing region 17, and the sample particles are directly injected into the center of the sample flow and confined therein. In this embodiment, the primary sheath flow channel does not branch into subchannels, and the acceleration of the sheath fluid and suspension of injected particles can be accomplished by shaping the primary sheath flow channel in a suitable manner.

Figure 6:
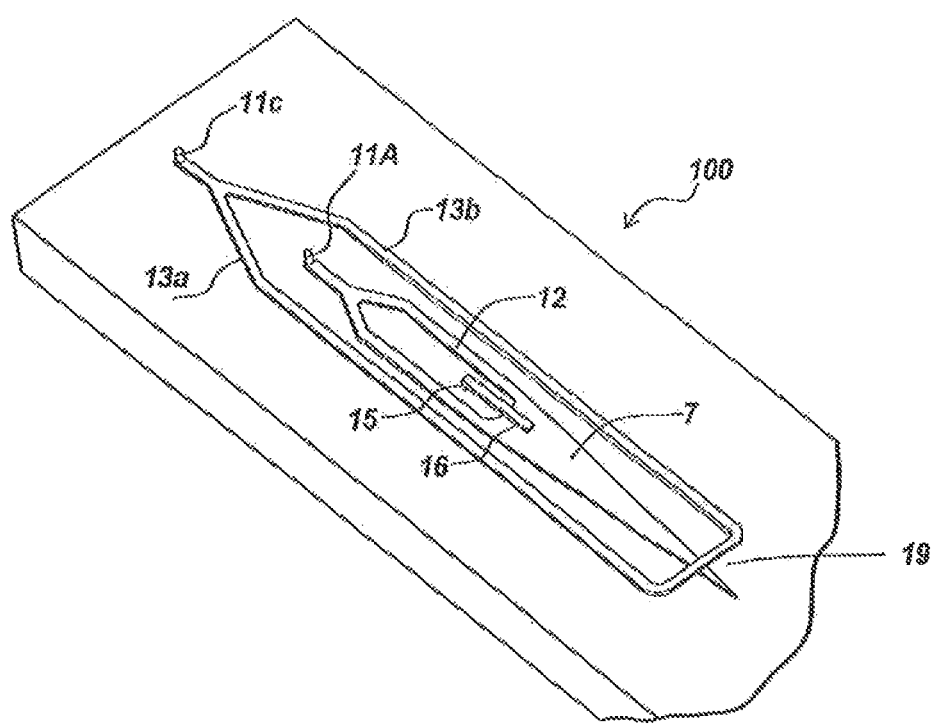
FIG. 6 is a perspective view of a sheath flow structure according to another embodiment of the invention.

FIG. 6 illustrates a sheath flow structure 100 according to another embodiment of the invention, including separate sheath inlets for the primary sheath flow and the sheath fluid (secondary sheath fluid) that is added to the sheath flow in the secondary focusing region 19. As shown, the sheath flow structure 100 of FIG. 5 includes a primary sheath inlet 11a for providing a primary sheath flow to suspend the injected sample particles and a secondary sheath inlet 11c for providing secondary sheath flow to focus the particles within the primary sheath fluid in the secondary focusing region. In the embodiment shown in FIG. 5, the primary sheath inlet 11c is formed in an upper substrate layer 10a and the secondary sheath inlet 11c is formed in a second substrate layer 10b, though one skilled in the art will recognize that the invention is not limited to this configuration.

Figure 7A:
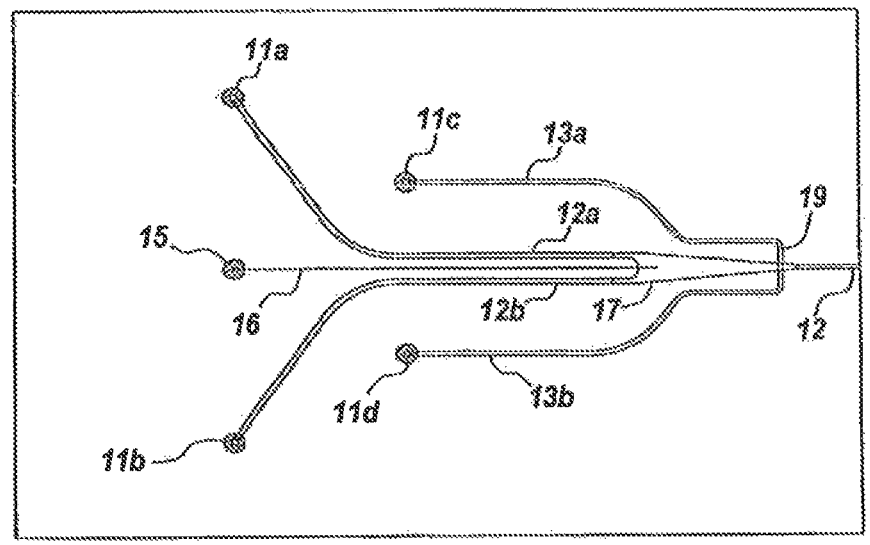
FIGS. 7A-7B illustrate a sheath flow structure including a sample inlet provided upstream of a sheath flow inlet according to another embodiment of the invention.
Figure 7B:
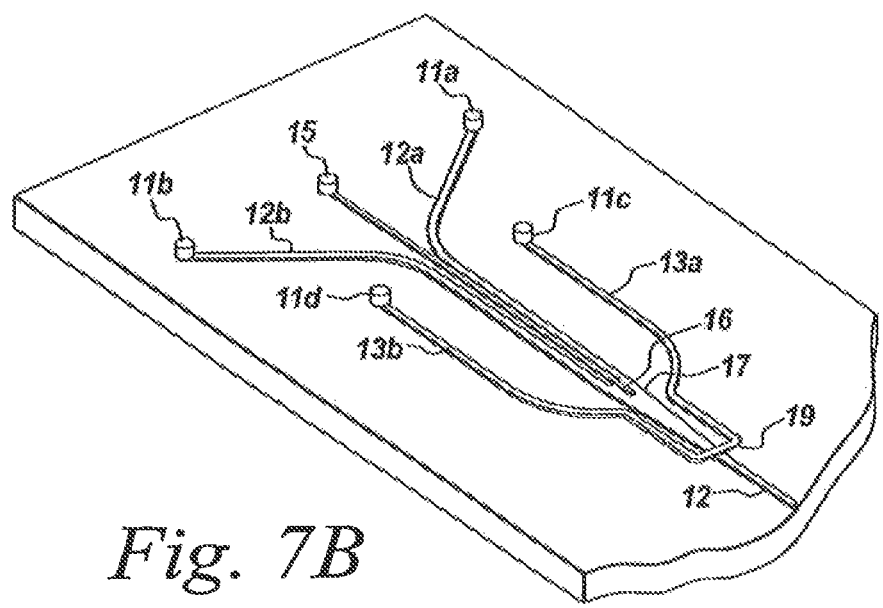

According to another embodiment of the invention, shown in FIGS. 7A and 7B, the sample inlet 15 may be provided upstream or behind the sheath inlet. In this embodiment, the upstream portion of the primary sheath flow channel 12 comprises two separate subchannels 12a, 12b, which converge in the primary focusing region 17. Each subchannel 12a, 12b has a separate inlet 11a, 11b for introducing sheath fluid to the respective subchannel. The embodiment of FIGS. 7A and 7B further includes separate sheath inlets 11c, 11d for the secondary sheath channels 13a, 13b. As described above, the secondary sheath channels intersect the primary sheath flow channel 12 in the secondary focusing region to provide focusing of a sample within a flowing sheath fluid in the primary sheath flow channel 12. The design of the illustrative sheath flow structure of FIGS. 7A and 7B is suitable for parallelization of the sheath flow process because multiple sample channels 16 can be fed into an array of sheath fluid injectors on a single microfluidic chip.

While the embodiment of FIG. 7 shows separate sheath inlets for each subchannel of the primary flow channel and each secondary sheath flow channel, one skilled in the art will recognize that the primary sheath flow channel can alternatively have a single inlet, as shown in FIGS. 2A-2C, 5A-5C and 6. The primary sheath flow channel can include subchannels that converge to suspend an injected particle, as described with respect to FIGS. 2A-2C and 6. The primary sheath flow channel may alternatively be shaped and configured to widen to surround an injected particle, as described with respect to FIGS. 5A-5C. In addition, while the embodiment of FIG. 7 shows the secondary sheath flow channels to be formed separately from the primary sheath flow channel, one skilled in the art will also recognize that one or more of the secondary sheath flow channels 13a, 13b may be formed by diverted a portion of the sheath fluid in the primary sheath flow channel into one or more of the secondary flow channels, eliminating the need for a separate sheath inlet.

Figure 8A:
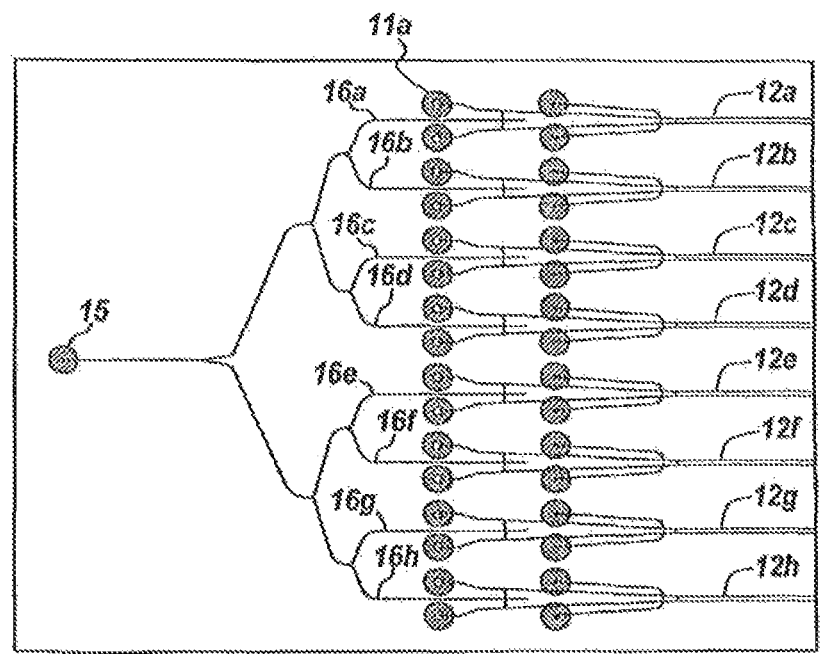
FIGS. 8A-8B illustrate a parallelized sheath flow system for producing sheath flow in multiple parallel channels according to another embodiment of the invention.
Figure 8B:
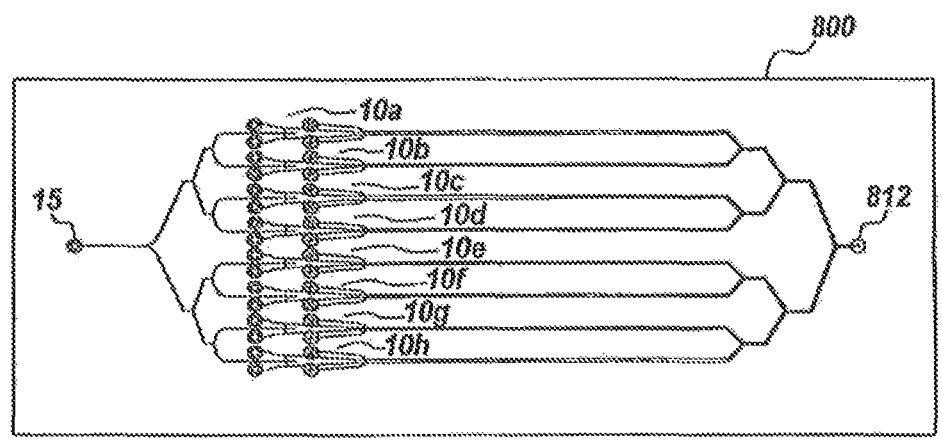

FIGS. 8A-8B illustrate an array of sheath flow structures 10a-10h may be formed on a single microfluidic chip 800 according to another embodiment of the invention. The microfluidic chip 800 can comprise an upper substrate layer including selected components of each sheath flow structure and a lower substrate layer including selected components of each sheath flow structures such that when the upper substrate layer is stacked on the lower substrate layer, the array of sheath flow structures is formed. FIG. 8 illustrates an array of eight parallel three-dimensional sheath flow structures 10a-10h implementing the rear sample injection scheme of FIG. 7. As shown, a single sample inlet 15 can be used to inject a sample into each of the primary sheath flow channels 12a-12h. The microfabricated design allows the system to precisely split an input sample provided in the sample inlet among eight separate sample channels 16a-16h, which then inject the sample into the primary sheath flow channels. The use of a sample inlet 15 upstream of the sheath inlet facilitates parallelization of multiple sheath flow structures in a single integrated system. Alternatively, a sample inlet provided upstream of the sheath flow inlets may be separately provided for each primary sheath flow channel.

Each of the channel inlets 11a, 11b, 11c or 11d for each sheath flow structure may be aligned, as shown in FIGS. 8A and 8B or staggered. Furthermore, a single inlet may be provided for one or more primary sheath flow channel and/or secondary sheath channel in each sheath flow structure in the parallelized system of FIG. 8, or the channels may share inlets, as described above.

In the embodiment shown in FIG. 8B, the primary sheath flow channels 12a-12h converge downstream of the secondary focusing regions, so that the sheath flows produced therein are rejoined and flowed off-chip via a single outlet 812. Alternatively, each primary sheath flow channel can separately flow off-chip.

Exemplification of the Invention

The parallelized sheath flow structure 800 of FIG. 8 was formed on a microfluidic chip and used to produce a sheath flow. Eight primary sheath flow channels were formed 800 microns apart, with associated sample channels, secondary sheath flow channels and other components also formed in parallel on the chip. The chip was glued to a fixture by 300LSE adhesive available from 3M Corporation and cured for 72 hours. A 10:1 dilution of 6 micron yellow beads from Spherotech was used as the sample and DakoCytomation sheath buffer was used as sheath fluid. The sheath fluid to sample ratio was 45:1. The flow rate was produced so that the number of beads flowing through a selected primary sheath flow channel was about 750 beads per second. The injected sample was divided among the eight sample channels and the sample portion in each sample channel was injected into the DakoCytomation sheath buffer flowing through the primary sheath flow channel associated with that sample channel. The sheath flow was initially focused from the sides and bottom of the channel in the primary focusing regions around the sample of each primary sheath flow channel. After the primary focusing, the sample flowed to the secondary focusing region where sheath fluid from the secondary sheath channels was injected to focus the sample in a vertical direction and form a core of the sample within each primary sheath flow channel.

The resulting sheath flow was then observed using a fluorescent microscope over a period of about eight seconds, and the results are shown in FIGS. 9A-10. FIG. 9A is an image of one of the primary sheath flow channels 12 in the system of FIG. 8, illustrating the side walls 111, 112 of the channel 12. FIG. 9B is a fluorescent microscope image of the same region of the channel as shown in FIG. 9A taken using the fluorescent microscope after the secondary focusing of the sample in the channel. The side walls, while not clearly visible in FIG. 9B are in the approximate same location within the Figure as are the side walls 111, 112 in FIG. 9A. The bright spot illustrates the concentration of the fluorescent beads 160 of the sample in the core ten microns of the two-hundred micron channel 12. FIG. 10 is a histogram of the image of FIG. 9B across axis —A-A— demonstrating the clean core flow produced by the sheath flow structure. The magnitude of the peak in the histograms reflects the amount of fluorescence observed for each location within the respective channel. As clearly shown in these Figures, the sheath flow structure 800 of the illustrative embodiment of the invention produces a sample-focused hydrodynamic sheath flow forming a central, focused core of sample 160 within a channel 12.

Figure 11:
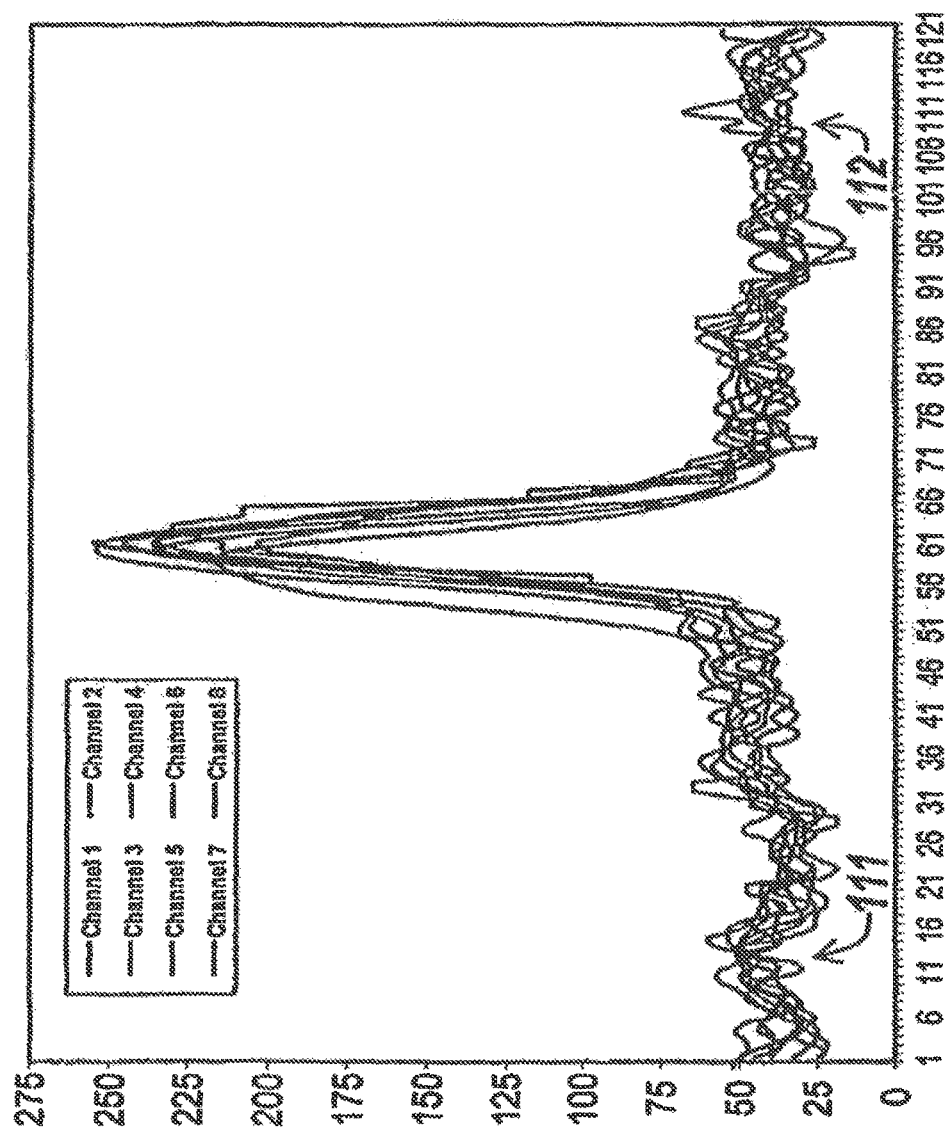
FIG. 11 is a histogram superimposing the fluorescence measurements from all eight primary sheath flow channels in the system of FIGS. 8A-8B.

FIG. 11 is a histogram comparing the cores for each of the resulting sheath flows in all eight samples of in the parallelized sheath flow structure of FIG. 8. As shown, each channel produces a substantially similar central core of the sample within the sheath fluid. The core is produced in substantially the same location within each primary sheath flow channel. The approximate locations of the side walls of the channels are indicated by reference numbers 111, 112.

Figure 12:
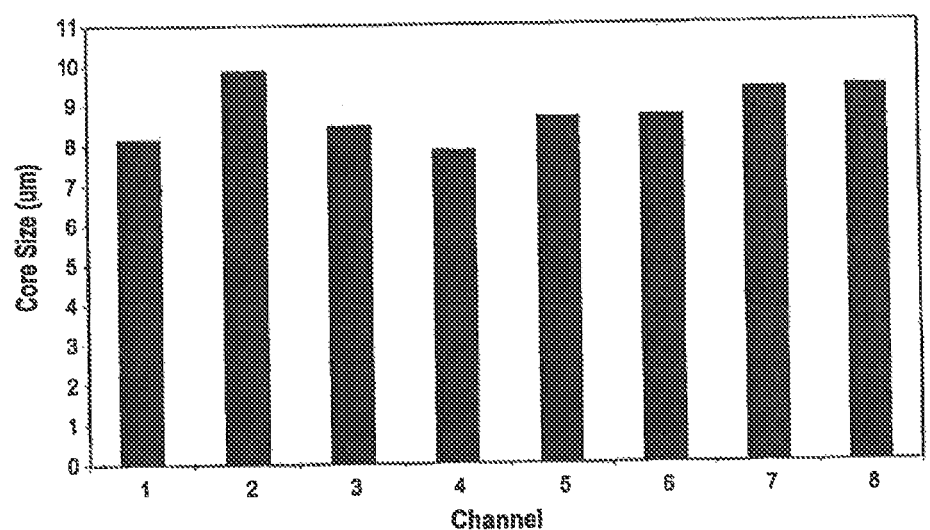
FIG. 12 illustrates the distribution of core sizes for the sheath flows produced in the primary sheath flow channels in the system of FIGS. 8A-8B.

FIG. 12 illustrates the distribution of core sizes from the single eight primary sheath flow channels in the test system of FIG. 8. As shown, the core produced in all of the channels using the sheath flow production method described above falls within 8.8+/−0.7 micron core width.

The sheath flow structure of the illustrative embodiment of the invention provides significant advantages not found in sheath flow structures of the prior art. The illustrative sheath flow structure provides three-dimensional hydrodynamic focusing using a single sheath fluid inlet. The illustrative sheath flow structure has a compact structure designed for manufacturability and requires only two structural layers in fabrication. Because the entrance to the sheath flow channels are only required on one side of the structure, the fluidic input/output structures can be simplified. Furthermore, the core flow vertical location is controllable by geometric (lithographic) resistance ratios between adjacent channels. The illustrative sheath flow structure provides accurate results that are largely insensitive to alignment between adjacent layers, as the only alignment required is to maintain the components in adjacent layers along the same centerline. The reentrant flow downstream of sample injection is then symmetric. In addition, the long path length of the branching upper sheath channels 13a, 13b results in negligible resistance ratio (therefore flow rate ratio) shift between two branch arms through misalignment of centerlines.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A microfluidic system comprising:
a substrate;
a sample fluid inlet provided on a surface of the substrate;
a sample fluid channel configured to receive sample fluid from the sample fluid inlet;
a first sheath fluid inlet;
first and second sheath fluid branch channels configured to receive sheath fluid from the first sheath fluid inlet;
a second sheath fluid inlet;
third and fourth sheath fluid branch channels configured to receive sheath fluid from the second sheath fluid inlet;
a first focusing region configured to receive sample fluid from the sample fluid channel and sheath fluid from the first and second sheath fluid branch channels; and
a second focusing region downstream of the first focusing region and configured to receive sample fluid and sheath fluid from the first focusing region and to receive sheath fluid from the third and fourth sheath fluid branch channels.

2. The system of claim 1, wherein the first focusing region is configured to symmetrically receive sheath fluid from the first and second sheath fluid branch channels relative to a centerline of the sample fluid flowing in the first focusing region.

3. The system of claim 1, wherein the second focusing region is configured to symmetrically receive sheath fluid from the third and fourth sheath fluid branch channels relative to a centerline of the sample fluid flowing in the second focusing region.

4. The system of claim 1, wherein the sample fluid inlet, the first sheath fluid inlet and the second sheath fluid inlet are all provided on the same surface of the substrate.

5. The system of claim 1, wherein the sample fluid channel, the first and second sheath fluid branch channels, and the third and fourth sheath fluid branch channels are formed when an upper substrate layer is stacked on a lower substrate layer.

6. The system of claim 1, wherein the first focusing region and the second focusing region are provided as portions of a primary flow channel, and wherein a width of the primary flow channel at an upstream end of the first focusing region is greater than a width of the primary flow channel at a downstream end of the second focusing region.

7. The system of claim 1, wherein the first focusing region and the second focusing region are provided as portions of a primary flow channel and wherein a cross-sectional flow area of the primary flow channel at the upstream end of the first focusing region is greater than a cross-sectional flow area of the primary flow channel at the downstream end of the second focusing region.

8. The system of claim 1, wherein the first focusing region is configured to receive sheath fluid to focus the sample fluid in a first direction, and wherein the second focusing region is configured to receive sheath fluid to focus the sample fluid in a second direction.

9. The system of claim 1, wherein the first focusing region is configured to receive sheath fluid to width-wise focus the sample fluid, and wherein the second focusing region is configured to receive sheath fluid to height-wise focus the sample fluid.

10. A microfluidic system comprising:
a substrate;
a sample fluid inlet provided on a surface of the substrate;
a sample fluid channel configured to receive sample fluid from the sample fluid inlet;
a sheath fluid inlet;
first, second, third and fourth sheath fluid branch channels configured to receive sheath fluid from the sheath fluid inlet;
a first focusing region configured to receive the sample fluid from the sample fluid channel and receive the sheath fluid from the first and second sheath fluid branch channels; and
a second focusing region downstream of the first focusing region configured to receive the sheath fluid and the sample fluid from the first focusing region and the sheath fluid from the third and fourth branch channels.

11. The system of claim 10, wherein the first focusing region is configured to symmetrically receive the sheath fluid from the first and second sheath fluid branch channels relative to a centerline of the sample fluid flowing in the first focusing region.

12. The system of claim 10, wherein the second focusing region is configured to symmetrically receive the sheath fluid from the third and fourth sheath fluid branch channels relative to a centerline of the sample fluid flowing in the second focusing region.

13. The system of claim 10, wherein the sample fluid inlet and the sheath fluid inlet are provided on the same surface of the substrate.

14. The system of claim 10, wherein the sample fluid channel and the first, second, third and fourth sheath fluid branch channels are formed when an upper substrate layer is stacked on a lower substrate layer.

15. The system of claim 10, wherein the first focusing region and the second focusing region are provided as portions of a primary flow channel, and wherein a width of the primary flow channel at an upstream end of the first focusing region is greater than a width of the primary flow channel at a downstream end of the second focusing region.

16. The system of claim 10, wherein the first focusing region and the second focusing region are provided as portions of a primary flow channel and wherein a cross-sectional flow area of the primary flow channel at an upstream end of the first focusing region is greater than a cross-sectional flow area of the primary flow channel at a downstream end of the second focusing region.

17. The system of claim 10, wherein the first focusing region is configured to receive sheath fluid to focus the sample fluid in a first direction, and wherein the second focusing region is configured to receive sheath fluid to focus the sample fluid in a second direction.

18. A microfluidic system comprising:

a substrate;

a sample fluid inlet provided on a surface of the substrate;

a sample fluid channel configured to receive sample fluid from the sample fluid inlet;

a first sheath fluid inlet and a first sheath fluid branch channel configured to receive sheath fluid from the first sheath fluid inlet;

a second sheath fluid inlet and a second sheath fluid branch channel configured to receive sheath fluid from the second sheath fluid inlet;

a third sheath fluid inlet and a third sheath fluid branch channel configured to receive sheath fluid from the third sheath fluid inlet;

a fourth sheath fluid inlet and a fourth sheath fluid branch channel configured to receive sheath fluid from the fourth sheath fluid inlet;

a first focusing region configured to receive the sample fluid from the sample fluid channel and receive the sheath fluid from the first and second sheath fluid branch channels; and a second focusing region downstream of the first focusing region configured to receive the sheath fluid and the sample fluid from the first focusing region and receive the sheath fluid from the third and the fourth branch channels.

19. The system of claim 18, wherein the first focusing region is configured to symmetrically receive the sheath fluid from the first and second sheath fluid branch channels relative to a centerline of the sample fluid flowing in the first focusing region, and wherein the second focusing region is configured to symmetrically receive the sheath fluid from the third and fourth sheath fluid branch channels relative to a centerline of the sample fluid flowing in the second focusing region.

20. The system of claim 18, wherein the first focusing region is configured to receive the sheath fluid to focus the sample fluid in a first direction, and wherein the second focusing region is configured to receive the sheath fluid to focus the sample fluid in a second direction.

* * * * *